(12) United States Patent
Wallace et al.

(10) Patent No.: US 6,759,028 B2
(45) Date of Patent: Jul. 6, 2004

(54) METHODS FOR TREATING AVM'S USING RADIOACTIVE COMPOSITIONS

(75) Inventors: George Wallace, Coto de Caza, CA (US); Richard J. Greff, St. Pete Beach, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 09/985,607

(22) Filed: Nov. 5, 2001

(65) Prior Publication Data

US 2002/0136688 A1 Sep. 26, 2002

Related U.S. Application Data

(63) Continuation of application No. 09/311,803, filed on May 13, 1999, now Pat. No. 6,333,020.

(51) Int. Cl.[7] .................. A61K 51/00; A61M 36/14
(52) U.S. Cl. .............. 424/1.25; 424/1.11; 424/1.33; 424/1.37; 514/944; 600/3; 600/4
(58) Field of Search ....................... 424/1.21, 1.11, 424/1.65, 9.1, 9.2, 9.3, 9.4, 9.5, 9.6, 1.33, 1.29, 1.25, 450, 489, 1.37; 600/450, 3, 4, 7.8; 604/264; 514/944, 937; 524/916; 252/625, 634, 315.01

(56) References Cited

U.S. PATENT DOCUMENTS

| | | |
|---|---|---|
| 3,527,224 A | 9/1970 | Rabinowitz et al. |
| 3,591,676 A | 7/1971 | Hawkins et al. |
| 4,708,718 A | 11/1987 | Daniels |
| 4,938,763 A | 7/1990 | Dunn et al. |
| 5,580,568 A | 12/1996 | Greff et al. |
| 5,667,767 A | 9/1997 | Greff et al. |
| 5,894,022 A | 4/1999 | Ji et al. |
| 5,895,411 A | 4/1999 | Irie |
| 6,015,541 A | 1/2000 | Greff et al. |
| 6,333,020 B1 * | 12/2001 | Wallace et al. ............ 424/1.21 |

FOREIGN PATENT DOCUMENTS

| | | |
|---|---|---|
| GB | 2014043 A | 8/1979 |
| WO | 89/11874 | 12/1989 |
| WO | 99/12577 | 3/1999 |
| WO | WO 00/66183 | 11/2000 |

OTHER PUBLICATIONS

Kinugasa, et al., "Direct Thrombosis of Aneurysms with Cellulose Acetate Polymer", *J. Neurosurg.*, 77: 501–507 (1992).
"CANCER, Principles & Practice of Oncology", 4th Ed., vol. 1, "Cancer Treatment", pp. 545–548 (1993).
Kinugasa, et al. "Early Treatment of Subarachnoid Hemorrhage After Preventing Rerupture of an Aneurysm", *J. Neurosurg.*, 83: 34–41 (1995).
Kinugasa, et al., "Prophylactic Thrombosis to Prevent New Bleeding and to Delay Aneurysm Surgery", *Neurosurg.*, 36: 661 (1995).
Taki, et al., "Selection and Combination of Various Endovascular Techniques in the Treatment of Giant Aneurysms", *J. Neurosurg.*, 77: 37–24 (1992).
Casteneda–Zuniga, et al., "Interventional Radiology", in Vascular Embolotherapy, Part I, 1: 9–32, Williams & Wilkins, Publishers (1992).
Ondra, et al., "The Natural History of Symptomatic Arteriovenous Malformations of the Brain: a 24–Year Follow–Up Assessment", *J. Neurosurg.*, 73: 387–391 (1990).
De Salles, et al., "Arteriovenous Malformation Animal Model for Radiosurgery: The Rete Mirabile", *Am J. Neuroradiol.*, 17: 1451–1458 (1996).
Grzyska, et al., "A Joint Protocol for the Neurosurgical and Neuroradiologic Treatment of Cerebral Arteriovenous Malformations: Indications, Technique, and Results in 76 Cases", *Surg. Neurol.*, 40: 476–484 (1993).
Killer, et al., "Radiosurgery Following Embolisation and/or Surgery of Brain AVM's", *Interventional Neuroradiology*, 2: 27–33 (1996).

* cited by examiner

*Primary Examiner*—Dameron L. Jones
(74) *Attorney, Agent, or Firm*—Foley & Lardner, LLP

(57) ABSTRACT

Disclosed are methods for treating AVMs in a mammal by use of a radiation composition.

9 Claims, No Drawings

METHODS FOR TREATING AVM'S USING RADIOACTIVE COMPOSITIONS

This application is a continuation application Ser. No. 09/311,803, filed on May 13, 1999, now U.S. Pat. No. 6,333,020.

BACKGROUND OF THE INVENTION

Field of the Invention

This invention is directed to methods for treating arteriovenous malformations (AVM) by use of radioactive compositions. Specifically, these methods entail the in vivo delivery of radioactive compositions which are delivered as a fluid to one or more vascular sites in the AVM. Subsequent solidification of this composition in the AVM results in vascular embolization to at least partially ablate the AVM as well as delivery of a controlled amount of radiation to further ablate the AVM and to inhibit regrowth of the AVM.

In one embodiment, the fluidic radioactive compositions employed in the methods of this invention comprise a biocompatible polymer, a biocompatible solvent and a radioactive agent which provides a sufficient dose of radiation to at least partially ablate the AVM. In another embodiment, the fluidic radioactive compositions employed in the methods of this invention comprise a biocompatible prepolymer, a radioactive agent and optionally a biocompatible solvent which provides a sufficient dose of radiation to at least partially ablate the AVM and to inhibit regrowth of the AVM.

References

The following publications, patents and patent applications are cited in this application as superscript numbers:

Dunn, et al., U.S. Pat. No. 4,938,763 for "Biodegradable In-Situ Forming Implants and Methods of Producing Same", issued Jul. 3, 1990

Kinugasa, et al., "Direct Thrombois of Aneurysms with Cellulose Acetate Polymer", *J. Neurosurg.*, 77:501–507 (1992)

"CANCER, *Principles & Practice of Oncology*", 4th Ed., Volume 1, "*Cancer Treatment*", pp. 545–548 (1993)

Greff, et al., U.S. Pat. No. 5,667,767, for "Novel Compositions for Use in Embolizing Blood Vessels", issued Sep. 16, 1997

Greff, et al., U.S. Pat. No. 5,580,568 for "Cellulose Diacetate Compositions for Use in Embolizing Blood Vessels", issued Dec. 3, 1996

Kinugasa, et al., "Early Treatment of Subarachnoid Hemorrhage After Preventing Rerupture of an Aneurysm", *J. Neurosurg.*, 83:34–41 (1995)

Kinugasa, et al., "Prophylactic Thrombosis to Prevent New Bleeding and to Delay Aneurysm Surgery", *Neurosurg.*, 3:661 (1995)

Taki, et al., "Selection and Combination of Various Endovascular Techniques in the Treatment of Giant Aneurysms", *J. Neurosurg.*, 77:37-24 (1992)

Evans, et al., U.S. patent application Ser. No. 08/802,252 for "Novel Compositions for Use in Embolizing Blood Vessels", filed Feb. 19, 1997

Castaneda-Zuniga, et al., *Interventional Radiology*, in Vascular Embolotherapy, Part 1, 1:9–32, Williams & Wilkins, Publishers (1992)

Rabinowitz, et al., U.S. Pat. No. 3,527,224 for "Method of Surgically Bonding Tissue Together", issued Sep. 8, 1970

Hawkins, et al., U.S. Pat. No. 3,591,676 for "Surgical Adhesive Compositions", issued Jul. 6, 1971

Ondra, et al., *J. Neurosurg.*, 73:387–391 (1990)

Ogilvy, Internet publication, http://neurosurgery.mgh.harvard.edu/v-s-93-4.1, "Combined Modality Treatment in the Management of Brain Arteriovenous Malformations (AVMs)"

Greff, et al., U.S. patent application Ser. No. 08/962,819, Radioactive Embolizing Compositions, filed Nov. 3, 1997

All of the above publications, patents and patent applications are herein incorporated by reference in their entirety to the same extent as if each individual reference was specifically and individually indicated to be incorporated herein by reference in its entirety.

State of the Art

An arteriovenous malformation (AVM) is a congenital disorder characterized by a complex, tangled web of arteries and veins. An AVM may occur in the brain, brainstem, or spinal cord of a mammal or may be at a peripheral site such as in the pelvic areas, limbs, lungs, etc. and is caused by abnormal development of blood vessels. The most common symptoms of AVM include hemorrhaging (bleeding) and, for AVMs of the brain, brainstem or spinal cord, seizures, headaches, and neurological problems such as paralysis or loss of speech, memory, or vision. The symptoms of AVMs are often due to circulatory "steal" or insufficiencies caused by the AVM.

AVMs, particularly those located in the brain or spine of mammals (humans), are difficult or dangerous to treat. Cerebral AVMs, for example, are most commonly discovered in young human adults aged 20–40 years. These lesions are usually detected in patients as the result of a seizure or hemorrhage. AVMs hemorrhage at a rate of 4% per year.[13] Approximately half of these hemorrhages will carry significant morbidity or mortality and, accordingly, the lifetime risk of hemorrhage can be substantial.

Treatment of AVMs has employed a team approach utilizing combined modality therapy.[14] Three modalities of treatment heretofore employed include endovascular introduction of tissue glues which occlude parts or all of the AVM, microsurgical techniques to remove the AVM or radiosurgery (focused radiation) to ablate the AVM. Combined modality therapies include a first reduction of the AVM via endovascular introduction of tissue glues followed by stereotactic radiosurgery where a focused beam of radiation is used on a one-time treatment basis at a dose of from about 10 to 30 Gy with an average dose of about 20 Gy. This radiation causes changes in blood vessel walls, and over the course of 2–3 years the remainder of the AVM can be obliterated. This technique is most effective in smaller lesions (diameters less than 2.5 cm). Obliteration rates of up to 85% have been reported by two years after treatment. The risk of injury to surrounding normal tissue (e.g., brain tissue) is significant and is dependent upon the dose and focus of the radiation used which is kept to minimal levels to prevent collateral damage to healthy tissue.

Notwithstanding the benefits of a team approach of combined modalities for the treatment of AVMs, such a team approach requires at least two separate medical procedures on the patient. Accordingly, simpler procedures to effect treatment of AVMs would be particularly beneficial.

SUMMARY OF THE INVENTION

This invention is directed to methods for treating AVMs by use of radioactive embolization compositions. These compositions are delivered to one or more vascular sites of the AVM in a mammal as a fluid, composition which solidifies in vivo to form a solid, coherent radioactive mass. The solidified mass embolizes the vascular site thereby ablating or obliterating at least part of the AVM and the radioactivity attendant with the composition results in further ablation or obliteration of the AVM and inhibits regrowth of the AVM. This combined approach reduces the number of steps required to effect treatment of the AVM thereby providing a one-step treatment regimen for treating AVMs while inhibiting regrowth of the AVM.

Accordingly, in one of its method aspects, this invention is directed to a method for treating an arteriovenous malformation in a mammal which method comprises:

(a) selecting a fluidic composition comprising a biocompatible polymer, a biocompatible solvent and a water insoluble radioisotope; and (b) injecting a sufficient amount of said composition into one or more vascular sites leading to or within the AVM under conditions wherein a solid mass is formed thereby ablating at least part of the AVM wherein the radioisotope is employed in an amount effective to further ablate the AVM and inhibit regrowth of the AVM.

Preferably the radioactive fluid composition employed in this aspect of the methods of this invention comprises:

(a) a biocompatible polymer;

(b) a biocompatible solvent; and (c) from about 0.1 to about 35 weight percent of a water insoluble radioisotope having a radioactive content of from about 0.1 microcuries to about 35 microcuries.

The biocompatible polymer employed in these compositions and methods can be either a biodegradable polymer or a non-biodegradable polymer but is, preferably, a non-biodegradable polymer.

In another aspect of this invention, the biocompatible polymer can be replaced with a biocompatible preprolymer and, when so used, the presence of the biocompatible solvent becomes optional. In this embodiment, this invention is directed to a method for treating an arteriovenous malformation in a mammal which method comprises:

(a) selecting a fluidic composition comprising a biocompatible prepolymer, a water insoluble radioisotope and optionally a biocompatible solvent; and (b) injecting a sufficient amount of said composition into one or more vascular sites leading to or within the AVM under conditions wherein a solid mass is formed thereby ablating at least part of the AVM wherein the radioisotope is employed in an amount effective to further ablate the AVM and inhibit regrowth of AVM.

Preferably the radioactive fluid composition employed in this aspect of the methods of this invention comprises:

(a) a biocompatible prepolymer;

(b) an optional biocompatible solvent; and (c) from about 0.1 to about 35 weight percent of a water insoluble radioisotope having a radioactive content of from about 0.1 microcurie to about 35 microcurie.

In a preferred embodiment of either of the method aspects, the amount and radioactive content of the radioisotope is sufficient to provide for a cumulative ionizing radiation dosage at the site of implantation in a mammalian subject of from about 3 to about 30 Gray (Gy) as measured at a distance approximately 2 millimeters away from the vessel wall adjacent the vascular site leading to or within the AVM wherein the solid mass was formed.

It is, of course, understood that both the activity of the radioactive element and dose of radiation delivered to the AVM varies widely due to the requirements of different AVMs, volume of tissue treated, etc. Evaluation of such factors to determine the appropriate activity of the radioactive isotope and the dose of radiation delivered is well within the skill of the art.

In a further preferred embodiment of either of the method aspects, the biocompatible solvent is dimethylsulfoxide (DMSO), ethanol, ethyl lactate or acetone.

In one embodiment, the radioisotope acts as a contrast agent to permit visualization of the composition during delivery (e.g., catheter delivery). Alternatively, a non-radioactive contrast agent is employed in combination with the radioisotope in order to ensure visualization.

DETAILED DESCRIPTION OF THE INVENTION

This invention is directed to methods for treating arteriovenous malformations (AVM) in mammals by use of radioactive compositions which methods entail the in vivo delivery of radioactive compositions which are delivered as a fluid to one or more vascular sites leading to or within the AVM. Subsequent solidification of this composition in the vascularature results in vascular embolization which occludes the blood vessel and removes the AVM from systemic circulation. In turn, such embolization ablates at least part of the AVM and delivers a controlled amount of radiation to further ablate the AVM and to inhibit regrowth.

However, prior to discussing this invention in further detail, the following terms will first be defined:

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art.[1,3] For example, Dunn, et al.[1] discloses the following examples of biodegradable polymers: linear-chain polymers such as polylactides, polyglycolides, polycaprolactones, polyanhydrides, polyamides, polymrethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers and combinations thereof. Other biodegradable polymers include, for example, fibrin, gelatin, collagen, etc.

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.[9]

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to about 64,000. The weight average molecular weight of the cellulose diacetate composition, as determined by gel permeation chromatography, is preferably from about 50,000 to about 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. For ease of injection, the ethylene vinyl alcohol copolymer composition is preferably selected such that a solution of 5 weight percent of the ethylene vinyl alcohol copolymer, 20 weight percent of a tantalum contrast agent in DMSO has a viscosity equal to or less than 60 centipoise at 20° C. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. Even more preferably, the copolymers employed herein comprise a mole percent of ethylene of from about 38 to about 48 and a mole percent of vinyl alcohol of from about 52 to about 62. These compositions provide for requisite precipitation rates suitable for use in the methods described therein.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 $\mu$m or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, ethyl lactate, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic and substantially non-immunogenic when used internally in the patient and which are substantially insoluble in blood. Suitable biocompatible prepolymers include, by way of example, urethanes, cyanoacrylates[10,11,12], $(C_1-C_6)$hydroxyalkyl $(C_1-C_6)$ alkacrylate (e.g., hydroxyethyl methacrylate), silicone prepolymers, and the like. The prepolymer can either be a monomer or a reactive oligomer$_{12}$. Preferably, the biocompatible prepolymer does not cause an adverse inflammatory reaction when employed in vivo.

The term "radioisotope" refers to naturally or non-naturally occurring water insoluble radioisotopes conventionally employed in nuclear medicine including, by way of example only, $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{52}$magnesium, $^{55}$iron, $^{32}$phosphorus, and $^{90}$strontium. Other radionuclides currently being produced for use in nuclear medicine include, for example, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$lindium, $^{52}$iron, $^{167}$thulium, $^{57}$nickel, $^{62}$zinc, $^{61}$copper, $^{201}$thallium, and $^{123}$iodine. Each of these isotopes can be made by standard techniques well known in the art. Additionally, radioisotopes which are water soluble or water reactable are typically used as water insoluble salts including, for example, organic salts thereof such as acetate salts, proprionate salts, etc. It is understood that the term "radioisotope" includes the elemental isotope as well as inorganic and organics salts, complexes and/or compounds thereof.

In one embodiment, radioisotopes having a sufficiently high atomic number so as to be radiopaque can be used to serve both as a source of radiation and as a water insoluble contrast agent for detection under fluoroscopy.

In another embodiment, a separate non-radioactive contrast agent is employed in conjunction with the radioisotope.

The term "absorbed dose" or "radiation dose" refers to the dose of radiation typically employed by the attending oncologist in treating AVMs. The radiation dose is defined in terms of energy deposited per unit mass, given in the following units: 1 Gray (Gy)=1 Joule per kilogram. In the past, the standard unit of radiotherapy was 1 rad, and 1 Gy=100 rads.

Compositions

The polymer or prepolymer compositions employed in the methods of this invention are preferably first prepared without radioactive agents by conventional methods whereby each of the components is added and the resulting composition mixed together until the overall composition is substantially homogeneous. Examples of radioactive compositions are described by Greff, et al.[15]

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Where a separate non-radioactive contrast agent is employed, sufficient amounts of this contrast agent are then added to the biocompatible solvent to achieve the effective concentration for the complete composition. Preferably, the composition will comprise from about 7 to about 40 weight percent of total contrast agent (non-radioactive contrast agent plus any radiopaque radioisotope) and more preferably from about 14 to about 30 weight percent and even more preferably about 22 weight percent.

The biocompatible solvent preferably comprises from about 40 to about 90 weight percent of the composition based on the total weight of the composition and more preferably about 50 to about 90 weight percent.

When a water soluble non-radioactive contrast agent is employed, the agent is typically soluble in the solution comprising the non-aqueous solvent and stirring is effected to render the composition homogeneous.

When a water insoluble non-radioactive contrast agent is employed, the agent is insoluble in the biocompatible solvent, and stirring is employed to effect homogeneity of the resulting suspension. In order to enhance formation of the suspension, the particle size of the water insoluble non-radioactive contrast agent is preferably maintained at about 10 $\mu$m or less and more preferably at from about 1 to about 5 $\mu$m (e.g., an average size of about 2 $\mu$m).

In one embodiment, a non-radioactive contrast agent having a particle size of less than 10 $\mu$m is prepared, for example, by fractionation. In such an embodiment, a non-radioactive water insoluble contrast agent such as tantalum, having an average particle size of less than about 20 $\mu$m, is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition can be heat sterilized and then stored preferably in sealed bottles or vials until needed.

Each of the polymers recited herein is commercially available or can be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions can be prepared by adding sufficient amounts of any non-radioactive contrast agent employed in the liquid (e.g., liquid prepolymer) to achieve the effective concentration for the complete prepolymer composition. Preferably, the total contrast agent (non-radioactive contrast agent plus any radiopaque radioisotope) will comprise from about 7 to about 40 weight percent of the prepolymer composition based on the total weight of the composition and more preferably from about 14 to about 30 weight percent and even more preferably about 22 weight percent.

When a non-radioactive contrast agent is used which is not soluble in the biocompatible prepolymer composition, stirring is employed to effect homogeneity of the resulting suspension. In order to enhance formation of the suspension, the particle size of the insoluble non-radioactive contrast agent is preferably maintained at about 10 $\mu$m or less and more preferably at from about 1 to about 5 $\mu$m (e.g., an average size of about 2 $\mu$m).

When the prepolymer is liquid (as in the case of cyanoacrylates or silicone), the use of a biocompatible solvent is not strictly necessary but may be preferred to provide for an appropriate viscosity, for an appropriate curing time, etc. in the composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the, total weight of the composition.

Suitable solvents include iodinated soy bean or poppy seed oil for cyanoacrylates and water for hydroxyacrylics such as hydroxyethyl methacrylate. In such cases, the oil acts both as a carrier for the prepolymer, a contrast agent and a polymerization time modifier. Other solvents include hexamethyldisiloxane which is preferaoly employed in conjunction with silicone.

In a particularly preferred embodiment, the prepolymer is a cyanoacrylate which is preferably employed in a 1:1 ratio with an iodinated oil. When so employed, the cyanoacrylate adhesive is selected to have a viscosity of from about 5 to about 40 centipoise at 20° C.

The radioisotope is preferably added to the otherwise complete composition immediately prior to the administration of the composition to the patient in order to reduce exposure of radiation to the clinician. In a preferred embodiment, the radioisotope is $^{192}$iridium, $^{198}$gold, $^{125}$iodine, $^{137}$cesium or $^{60}$cobalt. The radioisotope and its activity are preferably selected relative to the size and location of the AVM in the patient. This material may also be used as part of or the entire contrast agent to aid in the placement of the composition, usually by fluoroscopy, to cause ablation or obliteration of at least a portion of the AVM.

Treatment dosages of radiation employed in a particular patient are, of course, dependent upon the judgment of the attending clinician and nuclear medicine professional depending upon factors such as the type and severity of the AVM in the patient, the age, weight and general condition of the patient, the toxicity and/or side effects due to the radiation treatment and the like. Such factors are well known to the skilled artisan.

In any event, in this embodiment, sufficient levels of radiation are employed to effect obliteration of at least part of the AVM and to inhibit regrowth of the AVM.

In view of the above, the compositions described herein preferably comprise from about 0.1 to about 35 weight percent of a water insoluble radioisotope having from a radioactive content of from about 0.1 microcurie to about 35 microcurie. In another preferred embodiment, the amount and radioactive content of the radioisotope is sufficient to provide for a cumulative ionizing radiation dosage at the site of implantation in a mammalian subject of from about 3 to 30 Gray (Gy).

The solid mass formed by the methods of this invention is permanently placed within the patient.

Methods

The compositions described above can be employed in the treatment of AVMs in mammals. The treatment protocol includes assessing the AVM volume, determine the total radiation activity needed to treat the AVM and determine the vascular site or sites to deliver the compositions. Each of these steps is well known in the art.

When the polymeric composition is introduced in vivo, the biocompatible solvent diffuses rapidly into the body fluid and a solid, non-migratory precipitate or solid mass forms which precipitate is the water insoluble polymer and radioisotope encapsulated therein as well as any non-radioactive water insoluble contrast agent. Without being limited to any theory, it is believed that initially, a soft gel to spongy solid precipitate or solid mass forms upon contact with the body fluid.

When a prepolymeric composition is introduced in vivo, the prepolymer rapidly polymerizes in situ (preferably in less than 15 minutes and more preferably in less than 5 minutes) and a solid non-migratory mass forms which mass is the water insoluble polymer and radioisotope encapsulated therein as well as any non-radioactive water insoluble contrast agent.

In either case, a solid non-migratory radioactive mass forms in the AVM which embolizes at least a portion of the AVM. In addition, the radiation employed in the composition results in further ablation of the AVM and inhibits angiogenesis of new vascular growth.

Utility

The compositions described herein are useful in ablating AVMs. The composition is delivered to a vascular site leading to or within an AVM by known endovascular catheter techniques and is employed in a sufficient amount to embolize the vascular site thereby ablating at least a portion of the AVM. In addition, the level of radiation employed in the composition delivered is sufficient to further ablate at least a portion of the AVM and to inhibit regrowth of the AVM. The in situ delivery of a low dose of radiation per this invention permits sustained release of the radiation to site specific areas within the body thereby yielding a prolonged effect with minimal collateral damage. In addition, the relatively low dose of radiation employed permits more facile handling of the composition with minimal or no shielding due to low exposure to radiation by the attending clinician. Accordingly, these compositions find use in human and other mammalian subjects requiring treatment of AVMs.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeter |
| DMSO = | dimethylsulfoxide |
| EVOH = | ethylene vinyl alcohol copolymer |
| g = | gram |
| Gy = | gray (units for dose of radiation; 1 Gy = 1 J per kg = 100 rads) |
| kg = | kilogram |
| mg = | milligram |
| mL = | milliliter |
| ppm = | parts per million |
| $\mu$Ci = | microCurie |
| $\mu$m = | micron |

Example 1

The purpose of this example is to demonstrate the preparation of polymer compositions useful in this invention. These compositions were prepared using "cold" isotopes in order to illustrate the compatibility of the compositions and suitability for delivery in vivo, It is understood that "hot" compositions could be similarly prepared.

Specifically, an EVOH polymer composition was prepared as follows:

Composition 0.396 g EVOH (48 mole percent ethylene);

1.485 g micronized tantalum; and 4.95 mL DMSO.

After dissolution of the polymer at 50° C., 3 cc of this composition was then added to 0.03 g iridium powder (Aldrich Chemical Company, Milwaukee, Wis., USA, Catalog No. 20968-6, 99.9% purity, screened to <25 $\mu$m) to provide for a suspension comprising 0.4% by weight iridium ("cold" or non-radioactive). The resulting composition was then shaken for 4 minutes to disperse the insoluble materials. Immediately, 0.8 cc of the suspension was withdrawn via a 1 cc syringe through a 21 gauge needle. Three 0.1 cc aliquots were then injected into an excess of normal saline maintained at about 37° C. to generate the precipitate. The saline was then stirred for about 10 minutes whereupon the precipitate was examined for inner/outer consistency. In each case, a solid coherent precipitate formed in the saline.

The procedure set forth above was repeated twice. In the first instance, the amount of tantalum powder was changed to 14 weight percent and the amount of iridium powder was increased to 6 weight percent. In the second instance, the tantalum powder was removed from the composition and the amount of iridium adjusted to 20 weight percent. In each case, the total amount of tantalum/iridium was about 20 weight percent.

Both compositions, upon injection into saline, provided a solid coherent precipitate.

Example 2

The purpose of this example is to demonstrate the preparation of a prepolymer composition useful in this invention. This compositions was prepared using "cold" isotopes in order to illustrate the compatibility of the composition and suitability for delivery in vivo. It is understood that "hot" compositions could be similarly prepared.

Specifically, a cyanoacrylate prepolymer composition was prepared by adding 500 mg of iridium non-radioactive powder (Aldrich Chemical Company, Milwaukee, Wis., USA, Catalog No. 20968-6, 99.9% purity, screened to <25 $\mu$m) to 2 g n-butyl cyanoacrylate containing 100 ppm $SO_2$ as a stabilizer to yield a composition comprising 20% by weight of iridium. The ingredients mixed well, yielding a black/gray suspension. The iridium settled within several seconds after mixing, so constant, gentle agitation was required.

In this regard, a higher viscosity cyanoacrylate composition (e.g., using a cyanoacrylate oligomer) could be used to prolong the suspension time of the iridium or, alternatively, a smaller particle size of the iridium can be used.

The mixture remained liquid with no signs of premature polymerization when evaluated at one hour after mixing and again after 12 days thereby evidencing that the iridium was compatible in this composition.

About 0.2 cc of this composition was taken up in a 1 cc syringe through a 21 gage needle and injected into about 150 cc of an aqueous solution of 0.1 N $NaHCO_3$ to simulate a tissue environment and cure the prepolymer. Upon injection, three small black/gray droplets were formed which immediately fell to the bottom of the container. It took about 15 minutes for the cyanoacrylate to fully cure and to be tack free.

The procedure set forth above was repeated with the n-butyl cyanoacrylate alone (i.e., without the iridium) and the cyanoacrylate cured in approximately the same time evidencing that the iridium was compatible with the cyanoacrylate.

Example 3

The purpose of this example is to illustrate how to deliver the composition of either Example 1 or 2 to an AVM of a mammal. This example employs a pig and uses the recognized rete mirabele vasculature in the brain as the AVM model.

Specifically, a male pig (25 kg) is selected for use in this example. At this time, 1.0 mL of a 0.4% iridium composition described in Example 1 above (except that the iridium has a radioactive content of 15 $\mu$Ci and is added immediately prior to filling of the syringe and injection) is shaken to ensure homogeniety and then loaded into a 1 cc syringe. A compatible catheter such as an EasyRider™ catheter (available from Micro Therapeutics, Inc., Irvine, Calif., USA) is positioned at a vascular site 5 mm proximal to the rete mirabele with the aid of fluoroscopy to ensure proper positioning. Positioning of this catheter is achieved by femoral access then traversal through the carotid to the pharnygeal arteries. Approximately 0.2 mL of this composition is then injected into vasculature. Upon introduction into the vascular site, a solid coherent precipitate forms which comprises the polymer, the contrast agent and the iridium which solidifies in the blood vessel thereby ablating at least a portion of the blood vessel. This is confirmed with injection of contrast agent to visualize the lack of bloodflow thought the rete.

Over 30 days, the amount of radiation delivered internally to the AVM of the pig is about 15 Gy.

From the foregoing description, various modifications and changes in the composition and method will occur to those skilled in the art. All such modifications coming within the scope of the appended claims are intended to be included therein.

What is claimed is:

1. A method for treating an arteriovenous malformation in a mammal which method comprises:
    (a) selecting a fluidic composition comprising a biocompatible prepolymer, a water insoluble radioisotope and optionally a biocompatible solvent; and
    (b) injecting a sufficient amount of said composition into one of more vascular sites leading to or within the AVM under conditions wherein a solid mass is formed thereby ablating at least part of the then AVM
    wherein the radioisotope is employed in an amount effective to further ablate the AVM and to inhibit regrowth of the AVM.

2. The method according to claim 1 wherein said biocompatible prepolymer is selected from the group consisting of cyanoacrylates, urethanes, $(C_1-C_6)$hydroxyalkyl, $(C_1-C_6)$alkacrylate, and silicone prepolymers.

3. The method according to claim 1 wherein said biocompatible prepolymer is a cyanoacrylate.

4. The method according to claim 1 wherein said radioisotope is selected from the group consisting of $^{90}$yttrium, $^{192}$iridium, $^{198}$gold, $^{125}$iodine, $^{137}$cesium, $^{60}$cobalt, $^{55}$cobalt, $^{56}$cobalt, $^{57}$magnesium, $^{55}$iron, $^{32}$phosphorus, $^{90}$strontium, $^{81}$rubidium, $^{206}$bismuth, $^{67}$gallium, $^{77}$bromine, $^{129}$cesium, $^{73}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, $^{124}$iodine, and salts thereof.

5. The method according to claim 1 which further comprises a non-radioactive contrast agent.

6. The method according to claim 5 wherein said non-radioactive contrast agent is water soluble.

7. The method according to claim 6 wherein said water soluble non-radioactive contrast agent is selected from the group consisting of metrizamide, iopamidol, iothalamate sodium, iodomide sodium, and meglumine.

8. The method according to claim 5 wherein said non-radioactive contrast agent is water insoluble.

9. The method according to claim 5 wherein said water insoluble contrast agent is selected from the group consisting of tantalum, tantalum oxide, barium sulfate, tungsten, gold and platinum.

* * * * *

UNITED STATES PATENT AND TRADEMARK OFFICE
CERTIFICATE OF CORRECTION

PATENT NO. : 6,759,028 B2  
DATED : July 6, 2004  
INVENTOR(S) : George Wallace et al.

Page 1 of 1

It is certified that error appears in the above-identified patent and that said Letters Patent is hereby corrected as shown below:

Column 2,  
Line 3, after "U.S. patent application Ser. No. 08/962,818", please insert -- now U.S. Patent 6,015,541 --;  
Line 64, please remove the comma after "fluid";

Column 4,  
Line 38, replace "polymrethanes" with -- polyurethanes --;

Column 6,  
Line 49, replace "lindium" with -- indium --;

Column 8,  
Line 54, replace "preferaoly" with -- preferably --;

Column 12,  
Line 3, please insert -- the -- before "vasculature";  
Line 8, replace "thought" with -- through --;  
Line 31, please delete the comma after "hydroxyalkyl";

Signed and Sealed this

Eighth Day of March, 2005

JON W. DUDAS  
*Director of the United States Patent and Trademark Office*